United States Patent [19]

McCracken

[11] Patent Number: 5,369,527
[45] Date of Patent: Nov. 29, 1994

[54] MELANOMA DETECTION DEVICE

[76] Inventor: Robert McCracken, P.O.Box 287, Sand Lake, N.Y. 12153

[21] Appl. No.: 984,968

[22] Filed: Dec. 3, 1992

[51] Int. Cl.⁵ .......................................... G02B 27/02
[52] U.S. Cl. ................... 359/805; 359/442; 359/803
[58] Field of Search ................. 359/436–442, 359/802–812, 817, 818; 128/23; 422/104; 356/244, 245

[56] References Cited

U.S. PATENT DOCUMENTS

| | | | |
|---|---|---|---|
| 1,145,959 | 7/1915 | Amstutz | 359/441 |
| 1,803,483 | 5/1931 | O'Meara | 359/441 |
| 1,840,135 | 1/1932 | Schutt | 359/809 |
| 3,409,347 | 11/1968 | Vogel | 359/808 |
| 3,704,938 | 12/1972 | Fanselow | 359/806 |
| 4,090,501 | 5/1978 | Chaitin | 128/23 |
| 4,128,400 | 12/1978 | Mühlb/ck et al. | 359/809 |
| 4,435,912 | 3/1984 | Adrian et al. | 359/817 |
| 4,479,931 | 10/1984 | Lambrecht et al. | 424/1.1 |
| 4,568,184 | 2/1986 | Krantz et al. | 356/244 |
| 4,881,334 | 11/1989 | Brown | 40/365 |
| 4,940,311 | 7/1990 | Buszek et al. | 359/441 |
| 5,132,087 | 7/1992 | Manion et al. | 422/104 |

FOREIGN PATENT DOCUMENTS

| | | | |
|---|---|---|---|
| 83015 | 6/1980 | Japan | 389/809 |
| 93513 | 4/1990 | Japan | 359/807 |

*Primary Examiner*—Loha Ben
*Assistant Examiner*—Thong Nguyen
*Attorney, Agent, or Firm*—Marshall, O'Toole, Gerstein, Murray & Borun

[57] ABSTRACT

An apparatus and method for detecting indications of skin cancer, includes a magnifying glass for magnifying a lesion on an area of skin to be tested and indicia for determining the presence or absence of skin disease indications. The magnifying glass and the indicia are formed on a clear, flexible plastic sheet. The indicia include a circle for detecting whether the diameter of the lesion indicates the presence of melanoma and a cross for detecting whether the symmetry of the lesion indicates the presence of melanoma.

16 Claims, 1 Drawing Sheet

… …

MELANOMA DETECTION DEVICE

TECHNICAL FIELD

The present invention relates generally to cancer detection devices, and more particularly to a device for detecting skin cancer, specifically, melanoma.

BACKGROUND ART

Detecting cancer typically requires a series of complicated medical tests, including blood and tissue tests, wherein the number and type of tests are dependent on the type of cancer suspected. However, indications of skin cancer, specifically melanoma, can be detected visually. Such indications include lesions which are larger than a certain size, asymmetrical in shape, have irregular borders and/or consist of multi-colored tissue. In the past, there was no simple, single device to aid a physician in the visual recognition of skin cancer. Thus, to visibly recognize skin cancer and thereby to determine whether further tests were needed, a physician had to view the lesion carefully with a hand-held magnifying glass to determine whether it included irregular borders or multi-colored tissue and then had to measure the diameter and symmetrical properties of the lesion with a separate instrument having some sort of scale or ruler contained thereon. This was typically a very clumsy procedure to perform and, depending on the type of scale used, could be inaccurate. Likewise, for a doctor who was not experienced in detecting indications of melanoma or, for a lay person who was uninformed on the subject, there was no single device having means for measuring and detecting skin disease indications to determine whether diagnosis by an experienced physician was required.

Prior art devices including magnifying glasses are known. For example, a magnifying device having an attached scale for accurately measuring distances is shown in Amstutz, U.S. Pat. No. 1,145,959. Here, a magnifying glass is located above a surface containing a scale such that an object lying on the surface is magnified along with the scale to enable accurate magnified measurements. Other known magnifying devices suitable specifically for magnifying printed material include Brown, U.S. Pat. No. 4,881,334 and Buszek, et al. U.S. Pat. No. 4,940,311. None of these devices, however, includes a magnifying glass and means specifically adapted for the accurate and efficient measurement and detection of skin disease indications.

SUMMARY OF THE INVENTION

The present invention is directed to a device having a magnifying glass and indicia for measuring skin disease indications enabling a physician or a lay person to view a skin lesion and to determine indications of the presence or absence of cancerous tissue. The device is flexible so as to conform with any skin area thereby enabling an accurate determination of skin characteristics. The device avoids the inaccuracies present in other measuring devices, circumvents the clumsiness inherent in the use of multiple or non-flexible measuring devices and includes enough information printed thereon to enable use by an inexperienced operator.

In accordance with one aspect of the present invention, a skin disease detection apparatus includes means for magnifying an area of skin and means for detecting a visible skin disease indication. In the preferred embodiment of the invention, the magnifying means and the detecting means are integrally formed on a clear flexible plastic sheet. Preferably, the detecting means includes indicia printed or formed on the sheet that, when located adjacent an area of skin, are used to detect the presence or absence of a skin disease indication. Most preferably, the indicia may include a circle and a cross which are used to determine the diameter and the symmetrical properties, respectively, of a skin lesion. Also preferably, the sheet may include printing which indicates the relevant skin disease indications to be magnified by the magnifying glass or detected with the use of the indicia.

DESCRIPTION OF THE PREFERRED EMBODIMENT

Figure 1:
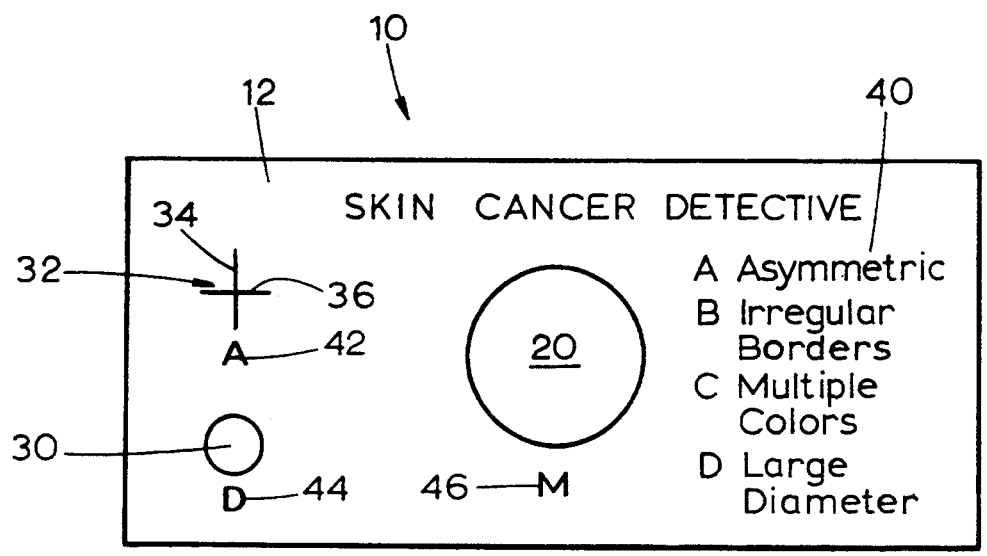
FIG. 1 is a plan view of a melanoma detection device according to the present invention.
Figure 2:
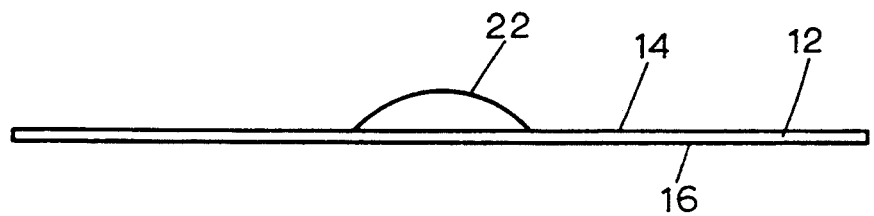
FIG. 2 is a side elevational view of the melanoma detection device.

Referring now to FIGS. 1 and 2 a melanoma detection device 10 according to the present invention is shown. The melanoma detection device 10 comprises a sheet 12 preferably constructed of a thin flexible material, for example, plastic. Also preferably, the sheet 12 is transparent. The sheet 12 has an upper flat surface 14 and lower flat surface 16 as shown in FIG. 2. The device 10 also includes a magnifier 20 having an upper convex surface 22 as shown in FIG. 2. The magnifier 20 magnifies objects placed adjacent to either the upper convex surface 22 or a portion of the lower flat surface 16 directly beneath the upper convex surface 22. Preferably, the magnifier 20 is constructed of the same material as sheet 12 and is integrally formed with sheet 12 to enable ease in manufacturing of the melanoma detection device 10.

The melanoma detection device 10 also includes indicia 30 and 32. Indicium 30 is a circle having a predetermined diameter while indicium 32 is a cross comprising intersecting lines 34 and 36 each having a predetermined length. Preferably, the lengths of lines 34 and 36 are equal, however, this condition is not absolutely necessary. The indicia 30 and 32 can be printed on the upper or lower surface 14, or 16, respectively, of sheet 12 or can be engraved or otherwise formed in sheet 12. Alternatively, the indicia 30 and 32 may extend fully through the sheet 12, in which case indicium 30 is a circular hole extending through sheet 12 while indicium 32 comprises slits extending fully through the sheet 12. Indicia 30 and 32 comprise means for detecting the presence or absence of a visible skin disease indication.

The melanoma detection device 10 also includes further indicia, formed, for example, by printing 40, comprising the words: "A Asymmetric"; "B Irregular Borders"; "C Multiple Colors"; and "D Large Diameter". An "A" is printed or otherwise formed directly beneath indicium 32 at a location 42, a "D" is printed or otherwise formed directly beneath indicium 30 at location 44 and an "M" is printed or otherwise formed directly below magnifier 20 at location 46. The printing 40 lists the four skin disease indications to be observed with the melanoma detection device 10. Furthermore, the "A" at the location 42 and the "D" at the location 44 correspond to the "A" and the "D" in the printing 40 and enable the user to determine the disease indication to be detected by each of the indicia 30 and 32. Thus, the symmetry of an area of skin is determined with the use of the indicium 32 while the diameter of an area of skin is determined with the use of the indicium 30.

The various steps described below may be performed in any order to check disease indications. In operation, the melanoma detection device 10 is placed adjacent to or in contact with an area of skin, usually a lesion, to be tested. When doing so, an operator may conform the flexible sheet 12 to the skin adjacent the lesion by bending or wrapping the sheet 12 around the skin as necessary to obtain as close a fit as possible between the melanoma detection device 10 and the lesion.

The operator may move the sheet 12 so that the indicium 30 is directly atop the lesion, placing the center of the lesion in approximately the center of the circular-shaped indicium 30. In this fashion, the operator may visually determine if the diameter of the lesion is larger or smaller than the diameter of the circular indicium 30. A lesion diameter larger than the indicium 30 indicates that one of the disease indications has been found and that, therefore, the lesion may be a melanoma.

Also, the operator may move sheet 12 so that the cross-shaped indicium 32 is atop the lesion such that the center of the lesion aligns approximately with the intersection point of the lines or slits 34 and 36. Once again, the operator bends the sheet 12 as necessary so that the sheet 12 lays flat on the lesion. In this fashion, the operator may determine the symmetry of the lesion by observing and comparing the lesion portions in the quadrants defined by the lines 34, 36. For example, if the end points of the line 34 lie directly on the edges of the lesion while one or both of the end points of the line 36 extend over the edge of the lesion, the lesion is asymmetrical. The operator can rotate the sheet 12 and thus the indicium 32 as necessary to observe the symmetry of the lesion at other points thereon, if desired.

The operator may further place the magnifier 20 above the lesion and view the lesion and the surrounding skin through the magnifier 20. In this manner, the operator can check for irregular lesion borders and for multiple-colored tissue within the lesion.

As noted above, the order in which the operator tests for the skin disease indications is not important. Therefore, the operator can use magnifier 20 first, the cross-shaped indicium 32 second and the circular-shaped indicium 30 third, or may use some or all of the elements 20, 30, 32 in a different order, if desired. Typically, the presence of one or more of the above-tested indications indicates a substantial probability of melanoma. It should be noted, however, that a large diameter in and of itself, is less a prediction of melanoma than the other abovementioned indications.

With the apparatus as described above, an experienced physician can quickly and efficiently determine whether a lesion is potentially a melanoma, and can therefore determine whether further tests are required. On the other hand, an inexperienced physician or a lay person can use the device to determine whether an experienced physician should be contacted to run more complete tests. This prevents costly medical bills arising from unnecessary physician consultation when there is little or no chance of the presence of melanoma. Specifically, the inexperienced physician and/or the lay person can refer to the printing 40 to determine the exact indications to look for in testing for melanoma and further, to determine which indicium to use in testing for each of the specific disease indications. This is accomplished by matching the letters in the printing 40 to the letters at locations 42 and 44.

In the preferred embodiment, the sheet 12 is approximately 12 centimeters long and 5 centimeters wide, while the magnification factor of the magnifier 20 is seven. It should be understood, however, that any size sheet 12 can be used and any magnification factor can be used so long as the magnification is great enough to enable an operator to determine whether multi-colored tissue or irregular borders are present in the lesion being tested. Also preferably, the circular shaped indicium 30 has an approximate diameter of 6 millimeters, the lines 34 and 36 of indicium 32 have an appropriate length of 12 millimeters and an approximate width of 0.5 millimeters, and the magnifier 20 has an approximate diameter of 25 millimeters.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

I claim:

1. A disease detection apparatus, comprising:
   means for magnifying an area of skin; and
   means for detecting a visible skin disease indication;
   wherein the magnifying means and the detecting means are integrally formed on a sheet made of a flexible material, wherein the detecting means includes first means for observing the diameter of a skin lesion and second means for observing a symmetrical property of a skin lesion and wherein the first observing means is circular and the second observing means is cross-shaped.

2. The apparatus of claim 1, wherein the magnifying means is a magnifier.

3. The apparatus of claim 2, wherein the flexible material is clear plastic.

4. The apparatus of claim 3, wherein the sheet includes print indicating relevant skin disease indications to be magnified by the magnifying means or detected by the detecting means.

5. An apparatus, comprising:
   a magnifier; and
   indicium located on a sheet connected to the magnifier for detecting the presence or absence of a disease indication;
   wherein the indicium includes a cross for observing a symmetrical property of a skin lesion.

6. The apparatus of claim 5, further including a circular-shaped indicium for observing the diameter of a skin lesion.

7. The apparatus of claim 6, wherein the magnifier and the indicium is integrally formed on the sheet.

8. The apparatus of claim 7, wherein the indicia are printed on the sheet.

9. The apparatus of claim 7, wherein the indicium is formed on the sheet.

10. The apparatus of claim 7, wherein the sheet is made of a flexible material.

11. The apparatus of claim 10, wherein the flexible material is clear plastic.

12. The apparatus of claim 5, wherein the magnifier is a magnifying glass.

13. The apparatus of claim 5, wherein the sheet includes print indicating relevant skin disease indications to be magnified by the magnifier or detected by the indicium.

14. A method of detecting indications of skin cancer on an area of skin comprising the steps of:

placing a magnifier included within a sheet over an area of skin to determine the presence or absence of a disease indication on the area of skin; and aligning the area of skin with an indicium included within the sheet to determine the presence or absence of another disease indication.

15. The method of claim 14, wherein the aligning step includes wrapping the sheet around the area of skin so that the indicium approximately conforms to the surface of the skin containing the area.

16. The method of claim 14 further including the step of aligning the area of skin with a second indicium included within the sheet to determine the presence or absence of another disease indication.

\* \* \* \* \*